(12) United States Patent
Hurley et al.

(10) Patent No.: US 7,718,832 B1
(45) Date of Patent: May 18, 2010

(54) COMBINATION CATALYTIC PROCESS FOR PRODUCING ETHANOL FROM SYNTHESIS GAS

(75) Inventors: Ronald G. Hurley, Sarasota, FL (US); Dennis Schuetzle, Grass Valley, CA (US); Matthew D. Summers, Auburn, CA (US)

(73) Assignee: Pacific Renewable Fuels, Inc., McClellan, CA (US)

( * ) Notice: Subject to any disclaimer, the term of this patent is extended or adjusted under 35 U.S.C. 154(b) by 44 days.

(21) Appl. No.: 11/966,711

(22) Filed: Dec. 28, 2007

Related U.S. Application Data

(60) Provisional application No. 60/882,792, filed on Dec. 29, 2006, provisional application No. 60/882,745, filed on Dec. 29, 2006.

(51) Int. Cl.
*C07C 29/141* (2006.01)
(52) U.S. Cl. .................................................... 568/869
(58) Field of Classification Search ................... 568/869
See application file for complete search history.

(56) References Cited

U.S. PATENT DOCUMENTS

| | | | |
|---|---|---|---|
| 4,122,110 A | 10/1978 | Sugier et al. | |
| 4,133,966 A | 1/1979 | Pretzer et al. | |
| 4,233,466 A | 11/1980 | Fiato | |
| 4,291,126 A | 9/1981 | Sugier et al. | |
| 4,386,009 A | 5/1983 | Feder et al. | |
| 4,423,257 A | 12/1983 | Isogai et al. | |
| 4,442,228 A | 4/1984 | Leupold et al. | |
| 4,472,526 A | 9/1984 | Cornils et al. | |
| 4,537,909 A | 8/1985 | Lin et al. | |
| 4,567,160 A | 1/1986 | Nay et al. | |
| 4,650,911 A | 3/1987 | Isogai et al. | |
| 4,725,626 A | 2/1988 | Graham et al. | |
| 4,727,200 A | 2/1988 | Wegman et al. | |
| 4,749,724 A | 6/1988 | Quarderer et al. | |
| 4,752,623 A | 6/1988 | Stevens et al. | |
| 4,758,600 A | 7/1988 | Arimitsu et al. | |
| 4,762,858 A | 8/1988 | Hucul et al. | |
| 4,935,547 A | 6/1990 | Leung et al. | |
| 5,783,607 A | 7/1998 | Chaumette et al. | |
| 6,248,796 B1 | 6/2001 | Jackson et al. | |
| 6,540,968 B1 | 4/2003 | Huang et al. | |
| 6,569,392 B1 | 5/2003 | Li et al. | |
| 7,071,141 B2 | 7/2006 | Gandhi et al. | |

OTHER PUBLICATIONS

Jiang et al. {Cuihua Xuebao (2000), 21(4), pp. 314-322; abstract only}.*
Chu et al. {Journal of Natural Gas Chemistry (1993), 2(4), pp. 290-301; abstract only}.*

* cited by examiner

*Primary Examiner*—Elvis O Price
(74) *Attorney, Agent, or Firm*—McKinney Law Group; Jeffrey A. McKinney

(57) ABSTRACT

A catalytic process selectively produces ethanol by contacting synthesis gas (syngas), composed primarily of hydrogen and carbon monoxide, with three catalysts within a reactor. The first catalyst is a hydrogenation promoter comprising Cu—Zn, Mo or Fe with an optional alkali metal additive and an optional support of aluminum oxide, silica, zeolite or clay. The second catalyst is a homologation promoter comprising one or more of the Group VIII metals in free or combined form with a co-catalyst metals consisting of Y or lanthanide or actinide series metals with optional additives and support. The third catalyst is a hydrogenation promoter. This series of catalysts improves the selectivity and yield for ethanol from syngas.

20 Claims, 4 Drawing Sheets

COMBINATION CATALYTIC PROCESS FOR PRODUCING ETHANOL FROM SYNTHESIS GAS

CROSS-REFERENCE TO RELATED APPLICATIONS

This application claims priority from U.S. provisional application Ser. No. 60/882,792 filed on Dec. 29, 2006, and from U.S. provisional application Ser. No. 60/882,745 filed on Dec. 29, 2006, each of which is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to a combination catalytic process for producing alcohols directly from synthesis gas (syngas) or any gas containing carbon monoxide and hydrogen. More particularly, the present invention pertains to a multi step catalytic process that promotes specific hydrogenation and homologation activities to improve the selectivity and yield of ethanol from a stream of syngas.

2. Description of Related Art

Global demand for energy continues to rise at a significant rate, particularly among developing industrialized nations. The increasing dependence of the United States on foreign sources of oil and natural gas and diminishing reserves have led energy producers to consider alternative or less conventional sources of energy for electricity production, domestic heating and transportation.

One source of energy that is available as an alternative to foreign sources of natural gas and petroleum in the United States is domestic coal. Coal continues to be an important source of fuel for electricity generation as well as a feedstock for chemical production. However, using coal as a primary source of fuel requires extensive processing to alleviate dust and gas emissions and other environmental concerns.

Converting coal into gas and other materials can also provide greater energy conversion efficiencies than found with traditional combustion in existing coal-fired power plants. Environmental pollutants may also be reduced over pulverized coal electricity production with the use of gasified coal.

The typical gasification process consists of placing coal in a vessel under high temperature and pressure and then introducing steam and oxygen into the vessel. The organic materials that are present in the coal are converted into carbon monoxide, carbon dioxide, hydrogen, and other carbon compounds. Other gases present include methane, and small amounts of ethane and propane. The combustible hydrogen and carbon monoxide components are typically separated from non-combustible water vapor, carbon dioxide and other gases. This mixture of combustible gasses from gasified coal is often referred to as synthesis gas or "syngas." Syngas may be used for combustion or as a feedstock for gas-to-liquid processes such as the Fischer-Tropsch process that produces valuable organic materials such as distillate fuels, naphtha and wax.

The high price of natural gas and oil has also caused the chemical industry in the United States to examine alternative feedstocks for the production of marketable chemicals. The chemical industry is the largest consumer of natural gas in the country and the substantial coal reserves make coal byproducts an attractive alternative to natural gas. Historically, coal gasification research has primarily focused on energy fuels and power production, with less emphasis on chemical production. For example, ethanol has been used as a fuel and as petroleum fuel additive that has the potential of reducing consumption and dependence on foreign oil. Adding ethanol to gasoline "oxygenates" the fuel mixture so that it burns more completely and reduces polluting emissions such as carbon monoxide. Brazilian domestic fuel, for example, currently contains at least 24% ethanol typically produced from sugar cane.

However, ethanol may also be used as a feedstock for the production of commodity chemicals. At the present time, much of ethanol that is not intended for human consumption is made synthetically, either from acetaldehyde made from acetylene, or from ethylene made from petroleum. Ethanol can also be oxidized to form acetaldehyde and then acetic acid and can be dehydrated to form ether. Ethanol is useful as a solvent for many substances and as a feedstock for many other organic compounds used in making perfumes, paints, lacquer, and explosives. For example, butadiene can be derived from ethanol that may be used in making synthetic rubber.

The technology for the production of syngas from various sources is well developed and advancements in production efficiency continue. Other sources of synthesis gas such as pyrolysis of wood and other agricultural waste and organic land fill waste are also under development. Unfortunately, present processes for the production of ethanol directly from syngas or any gas containing carbon monoxide and hydrogen do not have high selectivity for ethanol and are very complicated, inefficient and expensive processes.

Accordingly, there is an increasing need for a process that can directly convert syngas to ethanol with a high yield at relatively low cost. The present invention meets these needs as well as others and is a substantial improvement over the art.

BRIEF SUMMARY OF THE INVENTION

The present invention is a process for producing ethanol or other alcohols directly from synthesis gas with a combination catalyst that has high selectivity and high yields. The in-line reaction vessel apparatus shown schematically in FIG. 1 and functionally in FIG. 2 is used to illustrate the process of converting syngas to ethanol. Although a single reaction vessel is shown in FIG. 1, the three catalysts can be contained in separate reaction vessels connected in a series. Syngas is directed through the reaction vessel at a temperature preferably ranging from approximately 150° C. to 400° C. and at a pressure preferably ranging from approximately 200 psig to 2500 psig in this illustration.

According to one aspect of the invention, a process of preparing an alcohol with two or more carbon atoms is provided that first reacts a gas comprising carbon monoxide and hydrogen with a first catalyst configured to promote carbon monoxide hydrogenation. The gas from the first catalyst is then reacted with a second catalyst configured to promote alcohol homologation. Thereafter, the gas from the second catalyst reacts with a third catalyst configured to promote hydrogenation of acid and aldehyde byproducts to alcohols.

The reactions preferably occur under conditions of superatmospheric temperature and pressure.

According to another aspect of the invention, a process for the preparation of alcohols is provided comprising contacting a gas containing carbon monoxide and hydrogen with a first hydrogenation catalyst comprising Cu—Zn followed by contacting the outflow of gas from the first hydrogenation catalyst with a carbonylation catalyst comprising rhodium and a co-catalyst and then contacting the outflow of gas from the carbonylation catalyst with a second hydrogenation catalyst and a promoter while controlling the temperature and pressure of gas during contact with each of the catalysts.

It is a further aspect of the invention to provide a method for manufacture of ethanol from hydrogen and carbon monoxide with a reactor including:

(1) A hydrogenation catalyst containing Cu—Zn, Mo, Ni, or Fe;
(2) A carbonylation catalyst containing:
  (a) A Group VIII metal or mixture of Group VIII metals;
  (b) A co-catalyst metal of yttrium, a lanthanide and/or actinide series metal or mixtures thereof; and
(3) A second hydrogenation catalyst composed of Cu—Zn, Mo, Ni, or Fe.

The catalyst metals may be present as free metals, oxides, sulfides, carbides, carbonyls or mixtures thereof and can incorporate optional promoters and support compounds. Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Figure 1:
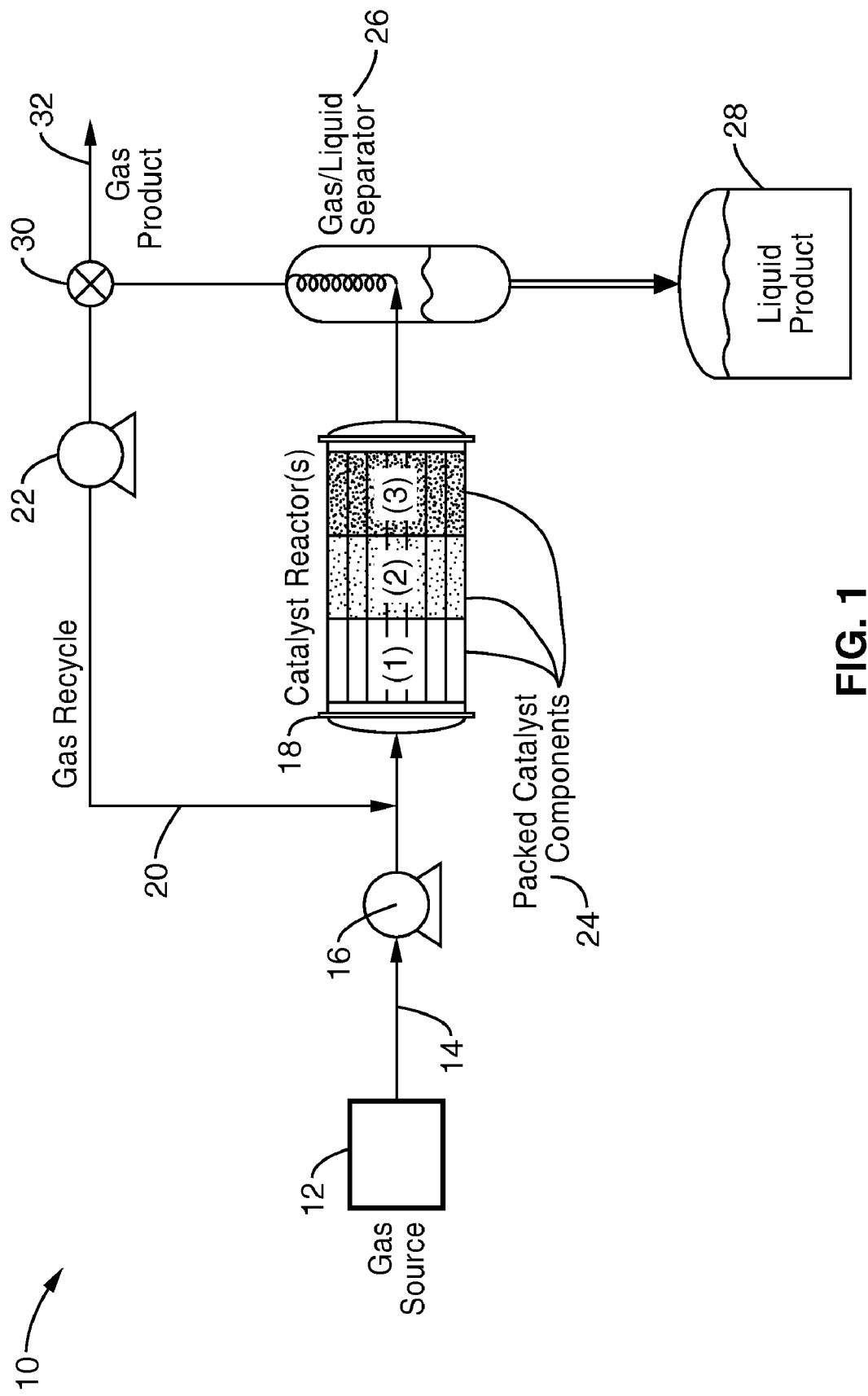
FIG. 1 is a schematic diagram of an illustrative reactor using a process for producing ethanol according to the present invention.
Figure 2:
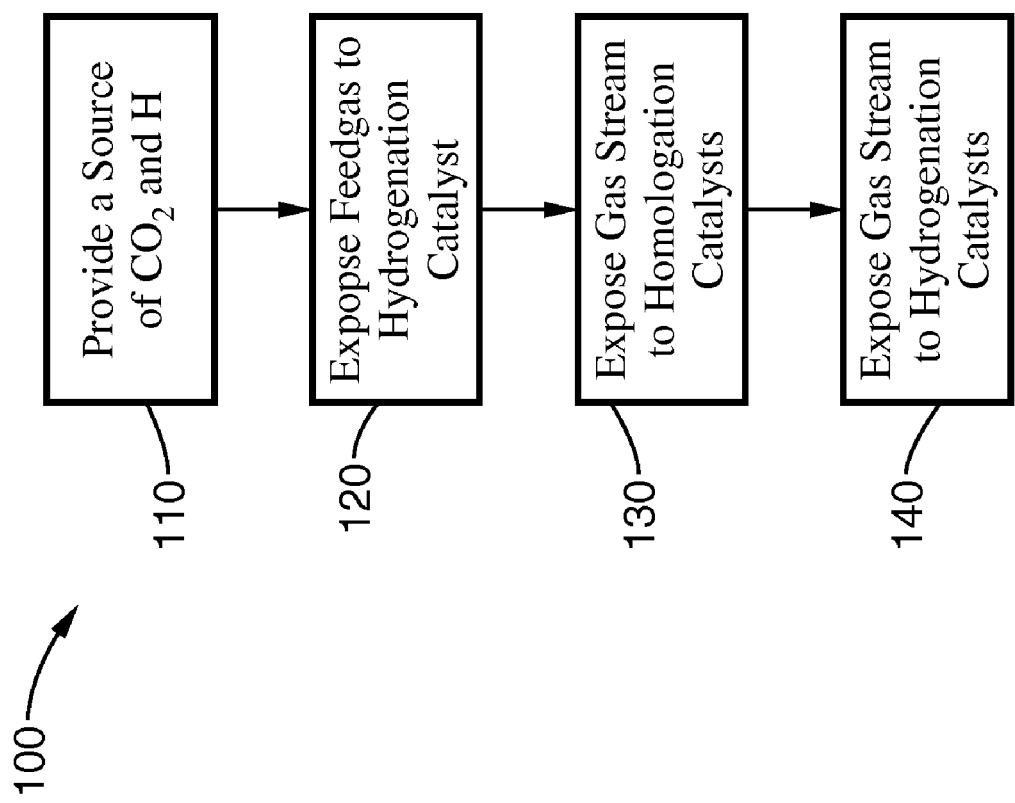
FIG. 2 is a flow chart of a process for producing ethanol from a gas containing carbon monoxide and hydrogen according to the present invention.

Referring more specifically to the drawings, for illustrative purposes the present invention is embodied in the apparatus shown schematically in FIG. 1 and the processes shown in FIG. 2 associated with the apparatus as described herein. Catalyst configurations particularly suited to the production of ethanol and method of manufacture are illustrated in FIG. 3 through FIG. 7 respectively. It will be appreciated that the apparatus may vary as to configuration and as to details of the parts, and that the methods may vary as to the specific steps and sequence, without departing from the basic concepts as disclosed herein.

A single reactor is schematically shown in FIG. 1 to illustrate the process for the production of ethanol from the reaction of carbon monoxide with hydrogen using a three-stage combination catalyst process according to the invention. The reactor system 10 is configured to be connected to a constant source of synthesis gas 12 from a variety of sources. Synthesis gas is defined as a gas comprising primarily carbon monoxide (CO) and Hydrogen ($H_2$) from any source. Typical synthesis gas from gasified coal or other carbonaceous fuels includes carbon monoxide, hydrogen and lesser amounts of carbon dioxide ($CO_2$) and other useful gases such as methane ($CH_4$) as well as small amounts of light paraffins, such as ethane and propane. It may also contain gases such as nitrogen, argon, helium, oxygen-containing compounds and water in a gaseous state. However, the preferred ratio of hydrogen to carbon monoxide is 0.1 to 10, and 0.2 to 5 by molar ratio is particularly preferred. Accordingly, the proportion of carbon monoxide and hydrogen together in the reactant gas is preferably about 20% to about 100% by volume.

The syngas feed 14 enters the system from any process that generates syngas or any storage source of gas containing significant amounts of hydrogen and carbon monoxide gas and the stream is compressed by a compressor 16 to approximately the desired reaction pressure that is in reactor vessel 18.

The reaction pressure can be low, namely approximately 200 pounds per square inch gauge (psig), because desired compounds can be manufactured at that pressure. However, higher pressures can be utilized in order to increase the space/time yield. Therefore, the preferred reaction pressure can vary between approximately 200 psig and approximately 2500 psig. A reaction pressure ranging from approximately 500 psig to approximately 1500 psig is particularly preferred.

The reaction temperature within reactor 18 preferably ranges from approximately 150° C. to approximately 400° C., with approximately 180° C. to approximately 325° C. particularly preferred. When a high reaction temperature is used, the formation of hydrocarbons as byproducts increases.

The syngas feed 14 may be combined with recycled gas 20 that has been compressed to the approximate pressure of the feed 14 by compressor 22. In the embodiment shown in FIG. 1, the combined gas feed enters the temperature controlled reactor vessel 18. However, the recycled gases could also enter the reaction vessel 18 separately. Although recycling of gas is shown in the apparatus of FIG. 1 for efficiency, it will be seen that the desired ethanol product can be produced with a single pass through the reactor.

Each reactor vessel 18 has catalyst components 24 combined in the same configuration as shown in FIG. 1 or may be in separate reactors. Generally, the preferred sequence of catalysts is a hydrogenation catalyst followed by a carbonylation catalyst and then a second hydrogenation catalyst.

The reactor vessel 18 may also include heating elements that permit the regulation of the temperature of the gas flowing through the reactor vessel 18 within the desired range of temperatures that will optimize the reactions. The reaction vessel 18 may also have temperature and pressure monitors to allow the regulation of the temperature and pressure of the gas stream through the reaction vessel 18. In one embodiment, the temperature and pressure in each of the three stages can be varied.

The feed rate of the reactant material gas relative to the volume of catalyst (also known as the gas hourly space velocity, GHSV, expressed under normal conditions of 0° C. and 0 psig) is between 100 and 40,000 hr$^{-1}$ (reciprocal hours) and is preferably adjusted for each catalyst component 24 and the reaction conditions to optimize ethanol production. Increasing the space velocity can increase yield and selectivity of the desired products but reduces the carbon conversion, requiring more recycling of the gas.

After passing though the catalysts 24 in reaction vessel 18, the outlet stream of gaseous products is directed to the gas/liquid separator 26. The gas-liquid separator is preferably a condenser but may be any other gas-liquid separator known in the art. The separated liquid 28 is collected and stored for further processing. The liquid product that is typically collected from syngas products from the reactor 18 is primarily ethanol with very small amounts of methanol, acetaldehyde, acetic acid and water. (See Table 1) The ethanol can then be purified using conventional methods of separation.

The remaining gases emerging from the gas/liquid separator 26 are preferably recycled for several cycles by compressing the gas stream as needed to approximately match the pressure of the syngas feed stream entering the reaction vessel 18. Valve 30 can be used to direct gas that has been cycled through the reaction vessel 18 several times to an exit line. It will be seen that the cycling of gases through the reactor effectively concentrates some of the useful gases such as methane that are produced by the process or are present in the syngas feed 14. Gas products 32 can be burned as a source of heat for the reactor, for example, or can be processed further as an additional feedstock for other chemical production.

The reaction equipment and conditions employed in the practice of the present invention are an appropriate combination in order to manufacture oxygen-containing compounds composed essentially of ethanol in high yield and with high selectivity while minimizing the formation of hydrocarbons. Reactor vessel 18 has a three stage combination catalyst composition that selectively processes syngas to ethanol.

Referring also to Table 1 and Table 2, the production of ethanol and other products from a single pass through a reactor is shown with different catalyst configurations at constant temperature and pressure. In the illustration shown in FIG. 1, the catalysts 24 of reactor vessel 18 are packed sequentially so that the gas stream encounters the catalysts sequentially. The catalysts are identified and described below and in Table 1 and Table 2 as catalyst components (1), (2), and (3).

The catalyst components can be contained in a flow type tubular reactor as shown in FIG. 1. In this embodiment, catalyst components (1), (2) and (3) or, various mixtures of the catalyst components (1), (2) and (3) are placed in the reactor in the proper sequence to establish a desired beneficial effect. Alternatively, catalyst components (1), (2) or (3) can be contained, either mixed or separate, in multiple reactors in a series.

Similarly, the catalyst components of the present invention can be adapted for use in a packed bed reactor, a fluidized bed reactor, or, alternatively, the catalyst components (1), (2), and (3) can be dissolved in solvents wherein the material gas is introduced to induce a reaction. Accordingly, reactors 18 with many different configurations can be used so long as the reactions take place in the proper sequence as described. Some blending of components (1) with (2) and (2) with (3) can also be beneficial to optimize performance.

Furthermore, recycling of gases through the reactor catalysts increases the concentration of methane, carbon dioxide in the product gases 32 and decreases the concentration of reactant gases, carbon monoxide and hydrogen through multiple passes through the catalyst reactor. Consequently, the efficiency and selectivity for ethanol is greatly improved with recycling. Therefore, product gases 32 that have been through several cycles of exposure to the reactor will typically include methane that has been effectively concentrated and can be processed further or burned as fuel.

The process steps for producing ethanol from syngas correspond to the catalyst components that are selected for the three stages in reactor 18 and are shown in FIG. 2. Turning now to FIG. 2, the process 100 for producing ethanol begins with a source of carbon monoxide and hydrogen at block 110. Suitable reactant gas preferably has a molar ratio of hydrogen to carbon monoxide is 0.1 to 10, and 0.2 to 5 molar ratio is particularly preferred as described previously.

At block 120, the carbon monoxide in the feed gas is hydrogenated. Catalyst component (1) is in the first stage of the reactor and is a catalyst that promotes carbon monoxide hydrogenation. Preferred embodiments include (a) a catalyst composed of Cu and Zn in free or combined form or (b) a catalyst containing Mo or Fe in free or combined form.

The primary chemistry involved in stage 1 at block 120 is detailed below. With catalyst component (1), the primary reaction is the hydrogenation of CO and $CO_2$ to form methanol. The relevant chemical reactions for the synthesis of methanol include the following:

$$CO + 2H_2 \leftrightarrow CH_3OH$$

$$CO_2 + 3H_2 \leftrightarrow CH_3OH + H_2O$$

$$CO + H_2O \leftrightarrow CO_2 + H_2.$$

In stage 2, the catalyst (2) promotes the homologation of methanol with hydrogen and carbon monoxide as shown in block 130. Preferred embodiments of catalyst (2) include a catalyst with one or more Group VIII metals (including Rh, Co, Ru, Os, Ir, Fe, Pt, Ni, Pd) in free or combined form with one or more co-catalyst metals including Yttrium (Y) or one of the lanthanide series (including La, Ce, Pr, Nd, Pm, Sm, Eu, Gd, Tb, Dy, Ho, Er, Tm, Yb, Lu) or the actinide series (including Ac, Th, Pa, U, Np, Pu, Am, Cm, Bk, Cf, Es, Fm, Md, No, Lw) in free or combined form.

At block 130, the primary activity of the catalyst is the homologation of methanol with carbon monoxide (CO) and Hydrogen ($H_2$) to produce higher carbon products with the use of catalyst component (2). Some of the key chemical reactions and products for the homologation of methanol include:

$$CH_3OH + CO + 2H_2 \leftrightarrow CH_3CH_2OH + H_2O$$

$$CH_3OH + CO + H_2 \leftrightarrow CH_3CHO + H_2O$$

$$CH_3OH + CO \leftrightarrow CH_3COOH$$

$$CH_3OH + 2CO + 4H_2 \leftrightarrow CH_3CH_2CH_2OH + 2H_2O$$

$$2CH_3OH + 2CO + 2H_2 \leftrightarrow CH_3COOCH_2CH_3 + 2H_2O$$

$$CH_3OH + H_2 \leftrightarrow CH_4 + H_2O$$

$$CO + H_2O \leftrightarrow CO_2 + H_2$$

In order to improve the selectivity for ethanol, catalyst component (3) is included to reduce other $C_2$ compounds to ethanol at block 140. Catalyst (3) promotes hydrogenation of carbon compounds. Preferred embodiments include (a) a catalyst composed of Cu and Zn in free or combined form or (b) a catalyst containing Mo or Fe in free or combined form.

The important chemical reactions for a hydrogenation step at block 140 following methanol homologation at block 130 include:

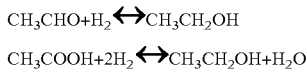

$$CH_3COOH + 2H_2 \leftrightarrow CH_3CH_2OH + H_2O$$

Referring also to Table 1, the selectivity and efficiency of the combination of catalysts for producing ethanol from syngas can be seen. When only catalyst component (1) is used, the main product is methanol and the yield and selectivity of ethanol are low. When only catalyst component (2) is used, the main products are acetaldehyde and ethanol, and the yields are also relatively low. When only catalyst components (1) and (2) are used, the main products are still acetaldehyde and ethanol, with increased yield but the selectivity for ethanol is still lower than desired. When only catalyst components (2) and (3) are used the selectivity for ethanol is improved but the conversion and yields are still low. On the other hand, when catalyst components (1), (2), and (3) are used in combination, as in the present invention, the yield and selectivity of ethanol is increased significantly making the overall combination an effective process to synthesize ethanol.

The catalyst components (1), (2) and (3) used in the present invention can be prepared in accordance with conventional methods used in the preparation of metal catalysts. For example, the catalyst components can be prepared with an impregnation method, an immersion method, an ion exchange method, a co-precipitation method or a kneading method known in the art.

In the preparation of catalyst components (1) and (3), the material compound used for copper or zinc can be a halide, a halogen acid salt, a nitrate, a hydroxide, an organic acid salt (e.g. a formate, an acetate or an oxalate) or the like. The material compound used for cobalt or molybdenum can be a halide, an inorganic acid salt (e.g. a halogen acid salt or a nitrate), an organic acid salt (e.g. a formate or an acetate), a carbonyl compound or the like. The material compound used for the alkali metal and other additives can be a halide, an inorganic acid salt (e.g. a nitrate or a chlorate), a hydroxide, an organic acid salt (e.g. a formate or an acetate), a metal alkoxide compound, an alkyl metal compound or the like. A metallic compound highly soluble in ethanol, water or any other appropriate solvent is preferred because the metal element contained in such a compound can easily be carried on a support.

In the preparation of the catalyst component (2), the material compound used for the Group VIII metal can be a compound which is ordinarily used in the preparation of a metallic catalyst, such as a halide (e.g. a chloride or a bromide), an inorganic acid salt (e.g. a nitrate or a carbonate), an organic salt or a chelate compound (e.g. an acetate, an oxalate, an acetylacetonate salt or an ethylenediamine acetate), a carbonyl compound, an amine complex salt, a metal alkoxide or an alkyl metal compound.

The material compound used for yttrium, lanthanide series and actinide series compounds can be a halide, an inorganic acid salt (e.g. a nitrate or a chlorate), a hydroxide, an organic acid salt (e.g. a formate or an acetate), a metal alkoxide compound, an alkyl metal compound or the like. A metallic compound highly soluble in ethanol, water or any other appropriate solvent is preferred because the metal element contained in such a compound can easily be carried on a support.

The catalyst components can also be prepared by other methods such as an ion exchange method wherein metals are supported by utilizing the ion exchangeability of the support, a co-precipitation method or a kneading method.

The catalyst components are ordinarily subjected to a reduction treatment for activation before they are used in reactions as a catalyst. The reduction is conducted at an increased temperature at which the components can be reduced preferably using a hydrogen-containing gas. Alternatively, the reduction may be conducted using another reducing agent such as a combination of carbon monoxide and water, hydrazine, a boron hydride compound or an aluminum hydride compound.

Turning now to FIG. 3 through FIG. 6, cross sections of four different embodiments of one catalyst configuration 210 for the production of ethanol of the invention are illustrated. In the embodiments shown, the catalysts are placed on a substrate 212 in different configurations. The catalyst components may be deposited or washcoated on a substrate 212, a mechanical carrier that is preferably made of an electrically insulating material that is stable at high temperatures, such as cordierite or mullite, etc. A mechanical carrier comprised of a monolithic magnesium aluminum silicate structure like cordierite is particularly preferred. It is preferred that the surface area of the monolithic structure provide be 1 or 2 $m^2/g$ is based on the adsorption of $N_2$ at liquid $N_2$ temperatures onto the internal surfaces of the carrier. Cell density may be maximized consistent with pressure drop limitations in the range of 200-1000 cells per square inch. A cell structure that would provide maximum residence time over the catalyst is optimum. The substrate may be provided in any suitable configuration, often being employed as a monolithic honeycomb structure, spun fibers, corrugated foils or layered materials. The substrate may also be beads, or pellets forming a bed depending on the application. In general, representative substrates include high surface area ceramic oxide supports, typically gamma aluminum oxide borne on a refractory substrate such as beads, pellets, or a monolithic substrate. Silica or alumina beads and monoliths are suitable which may be either a refractory metal oxide such as cordierite, or the like, or a high temperature oxidation resistant metal such as Fecralloy. The support has a preferred surface area ranging from ~100-1,000 $m^2/g$ with a minimum support pore diameter of approximately 10 Angstroms. Particular examples of the support include silica, a silicate, alumina, titania, activated carbon, an oxide of a metal, a metal, a zeolite, diatomaceous earth, clay etc.

The weight percent of each constituent element in the hydrogenation catalyst component has a preferred range. The weight percent of copper to support is approximately 0.001% to 50% and preferably approximately 0.01% to 20%, depending on the specific surface area of the support. The ratio of zinc to copper ranges from 0.01 to 50, preferably 0.1 to 5 by molar ratio. The ratio of any alkali metal promoter to copper ranges from 0.0001 to 5, preferably 0.001 to 3 by molar ratio.

The weight percent of molybdenum or iron to support may be within the range of 0.0001 to 1, preferably 0.001 to 0.5 by weight ratio, depending on the specific surface area of the support. The ratio of any alkali metal promoter to molybdenum is 0.0001 to 5, preferably 0.001 to 3 by molar ratio.

The ratio of each constituent element in the homologation catalyst components also has a preferred range. The weight percent of Group VIII metals to support is 0.0001 to 1, preferably 0.001 to 0.5, depending on the compound and the specific surface area of the support substrate 212. The ratio of yttrium, lanthanide series, or actinide series metal to Group VIII metal is 0.001 to 50, preferably 0.005 to 20 by molar ratio. The ratio of any alkali or other metal promoter to Group VIII metal may be within the range of 0.0001 to 10, preferably 0.001 to 5 by molar ratio.

Figure 3:
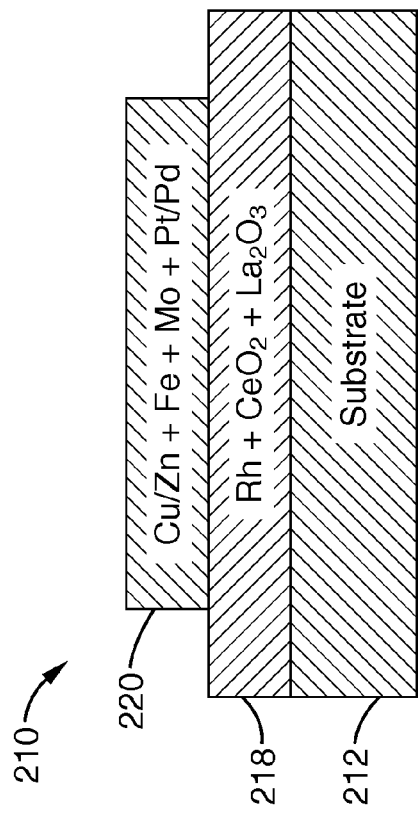
FIG. 3 is a schematic diagram of a cross section of a catalyst with minimal Rh and rare earth promoters in an outer layer according to the present invention.

In the embodiment shown in FIG. 3, a base layer of catalyst 214 is deposited on the substrate 212. In the embodiment shown, the base catalyst layer is a mixed metal oxide of Cu—Zn, Mo, Fe and precious metals Pt or Pd. A second layer of catalyst 216 is deposited over the first layer of catalyst 212. The catalyst of second layer 216 is an oxide coating of cerium oxide ($CeO_2$) and lanthanum oxide ($La_2O_3$) in the illustration shown in FIG. 3. Rhodium may be incorporated with the rare earth metal oxides or applied as a separate outer layer.

Figure 4:
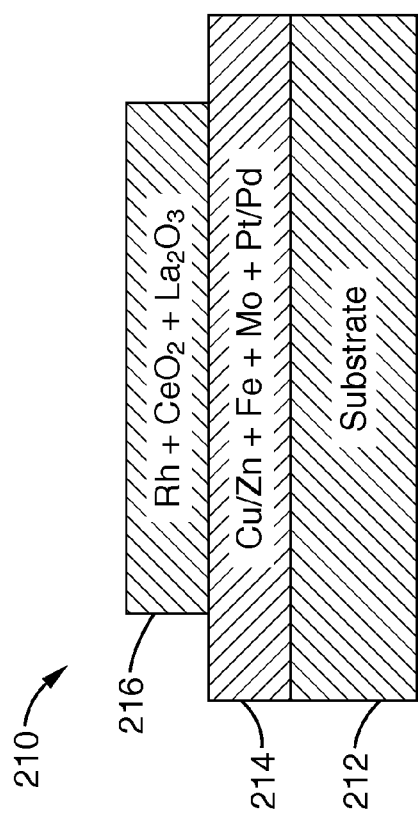
FIG. 4 is a schematic diagram of an alternative embodiment of a catalyst cross section with a minimal Rh and rare earth promoters in an inner layer according to the invention.

Alternatively, the embodiment shown in FIG. 4, the layers of mixed metal oxides and rare earth promoters are reversed from that shown in FIG. 3. A layer 218 of cerium oxide ($CeO_2$) and lanthanum oxide ($La_2O_3$) with rhodium is applied to the substrate 212. A layer 220 of Cu/Zn+Fe+Mo+Pt/Pd is provided on the coating 218, in any order individually or as mixture, e.g. as from a common solution by impregnation. In another embodiment, rhodium is applied as a separate outer layer is provided on top of the Cu—Zn layer. The rhodium acts as a broadening promoter to increase conversion efficiency.

Figure 5:
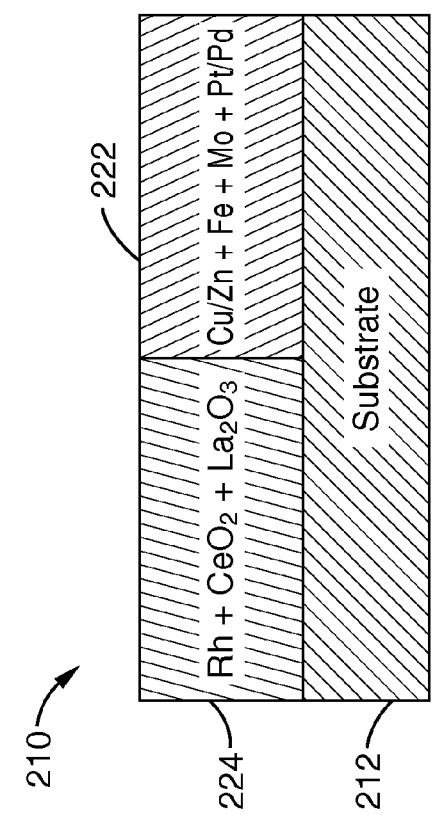
FIG. 5 is a schematic diagram of an alternative embodiment of a catalyst cross section with a zone design on single catalyst zoned as 50% with each catalyst material in a separate zone according to the invention.

In FIG. 5, the substrate 212 is coated with catalysts in zones 222, 224 in order to take advantage of conversion efficiencies for hydrogenation as well as homologation. One zone 222 has the mixed metal oxide Cu/Zn+Fe+Mo+Pt/Pd and the second zone 224 has the rare earth promoters. For example, the zones on a substrate can be 50%, 25% or 75% of the mixed oxides. In this case the rhodium is incorporated with the $CeO_2+La_2O_3$ to decrease the amount of rhodium that is needed and used.

Figure 6:
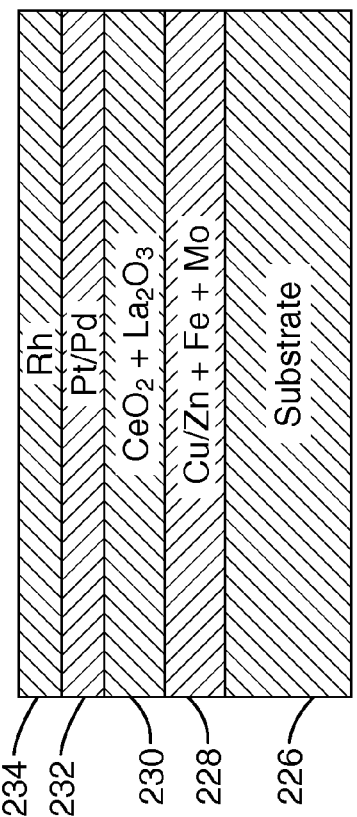
FIG. 6 is a schematic diagram of a cross section of catalyst with layers of mixed metal oxide particulates overlaid with precious metals and rhodium according to the invention.
Figure 7:
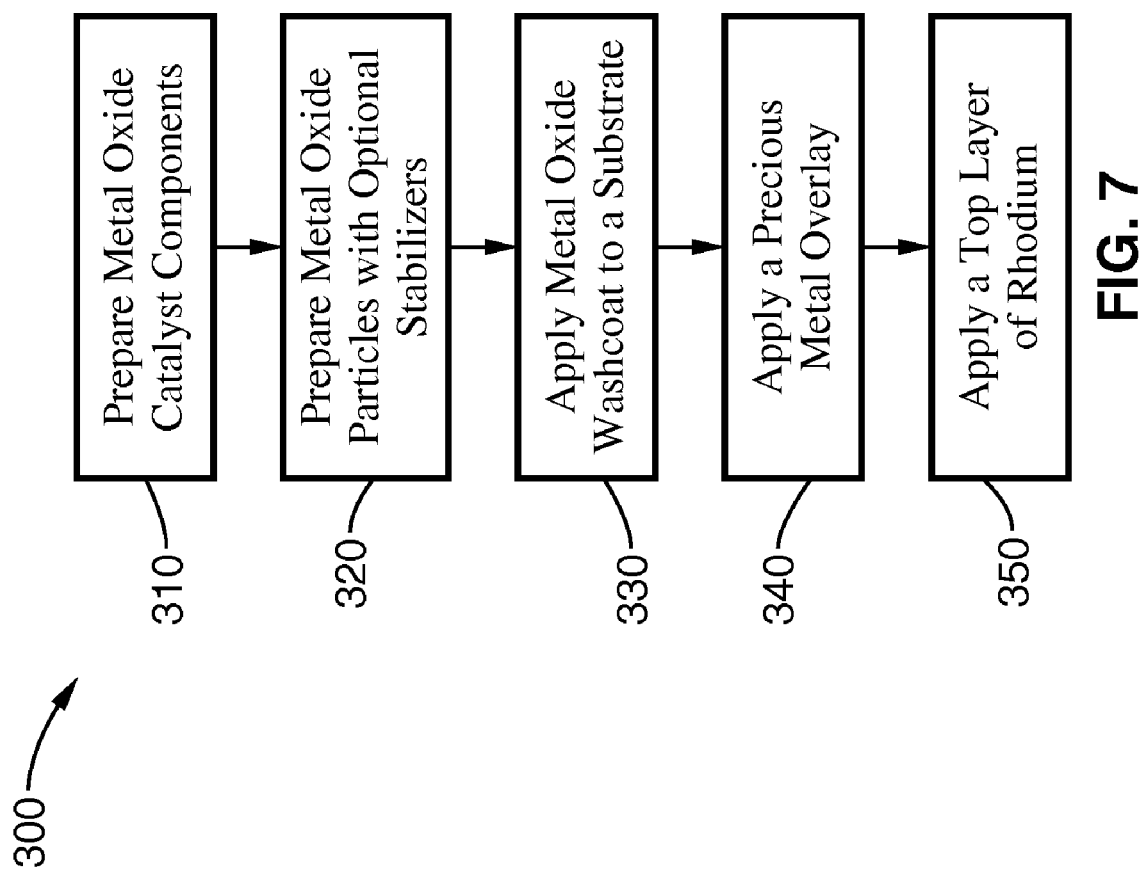
FIG. 7 is a flowchart of one method for manufacturing one embodiment of a catalyst of the present invention shown schematically in FIG. 6.

Referring also to FIG. 6 and FIG. 7, the oxide layers applied to the substrate are preferably coatings of previously formed metal oxide particles. Precious metals and rhodium are then applied to the oxide layers. As seen in the embodiment of FIG. 6, particulates of metal oxides are coated on a substrate 226. Although two layers of metal oxide particulates are shown in FIG. 6, it will be understood that more than two types of mixed metal oxide particulates can be applied to the substrate and several coatings of the same oxide particulates can be applied.

In the embodiment shown in FIG. 6, a first layer 228 of hydrogenation catalyst mixed metal oxide particulates of Cu—Zn, Fe or Mo is disposed on the substrate 226. In one embodiment, the mixed metal oxide particulates of layer 228 include a precious metal such as platinum, palladium or nickel within the oxide.

A second layer 230 of mixed metal oxide particulates is applied over the first layer of particulates 228 on the substrate 226. The mixed metal oxide of the second layer of particulates has at least one rare earth metal or yttrium. In one embodiment, rhodium is incorporated in the rare earth metal oxide layer of particulates 230.

A layer 232 of at least one precious metal such as platinum, palladium or nickel alone or in combination is applied over the top of the second mixed metal oxide layer 232. The application of precious metals may be reduced or eliminated if precious metals are made part of the oxide particulates. Likewise, one precious metal may be part of the oxide particulates and a different precious metal may be applied as an overlay.

A top layer 234 of rhodium may be applied over the precious metal layer 232. As with the precious metals, the quantity of rhodium may be reduced or eliminated if rhodium is made part of the mixed metal oxide particulate layer 230. The precious metal layer 232 and the rhodium layer 234 are preferably sprayed particles.

Although the layers of mixed metal oxide shown in FIG. 6 had top and bottom layers on the substrate 226, it will be understood that top and bottom layers of mixed metal oxide can be switched or applied in zones as illustrated schematically in FIG. 5. In addition, the mixed metal oxide layers 228, 230 may also include optional oxide stabilizers. For example, one embodiment of the invention comprises coating a substrate with oxide particles comprising (a) a mixed metal oxide of Cu—Zn, Mo, and Fe and, optionally, (b) 0 to 8 wt. % oxide stabilizers based on the weight of the mixed metal oxide. The oxide is coated on the substrate in an amount of 10-30 wt. % based on the weight of the substrate. A second oxide coating of particles including rare earth metals such as cerium (Ce) and lanthanum (La) in the form of $La_2O_3$, Ce as $CeO_2$ is applied to the first metal oxide layer. As indicated the catalyst metals may be present as free metals, oxides, sulfides, carbides, carbonyls or mixtures. A precious metal is deposited on the oxide coating, wherein first at least either Pt or Pd are deposited and them an small amount of Rh is deposited as an outer layer, in an amount of 1-2 $g/ft^3$ based on the volume of the support.

Referring specifically to FIG. 7, one method 300 for manufacturing a three way catalyst to provide high selectivity and yield for ethanol from syngas feedstock is shown. At block 310, the metal oxides are produced according to functional formulations to provide hydrogenation and homologation activity. Preferred hydrogenation catalyst embodiments include a catalyst composed of Cu and Zn in free or combined form or a catalyst containing Mo or Fe in free or combined form or a combination of all four.

The metal oxides prepared at block 310 can also include precious metals such as platinum, palladium and nickel as well as other metals including rhodium within the oxide. Precious metals can also be applied as a separate layer on top of an oxide layer as shown in FIG. 3 through FIG. 6.

The prepared metal oxides may be particularized and optionally mixed with oxide stabilizers at block 320 of FIG. 7. The mixed metal oxide is mixed with the stabilizers, e.g., as by milling in a slurry or similar process. Examples of such oxide stabilizers include thermal stabilizers, like titanium, zirconium or barium oxide and structural oxide stabilizers including titanium and calcium oxide. Optimally, the mixed metal oxide particles are mixed to form a substantially uniform mixture with stabilizer for the mixed metal oxide.

In forming the washcoat to be applied to the substrate at block 330, the size of the particles of mixed metal oxide and stabilizer materials (when included) is on average, less than approximately 1000 Angstroms in diameter ranging from about 200 to 900 angstroms in average diameter. Particle sizes of between approximately 500 angstroms to approximately 700 angstroms are particularly preferred. As the particle size of the washcoat particles decreases, the catalyst is more efficient in contacting the feed gas.

Each metal oxide washcoat can be applied at block 330 to a substrate structure that is typical for reactors that process a flow of gas. The substrate structures are preferably stable in high temperatures and electrical insulators such as cordierite or mullite, etc. Although such structures are preferred, the catalysts can be applied to essentially any substrate surface.

Several techniques for providing a particulate oxide washcoat on a substrate exist. Typically, slurries of the mixed metal oxide particles and optionally stabilizer particles are coated on a substrate by dipping or spraying and the excess material is generally blown off with air. Several coatings of the substrate in the washcoat may be necessary to develop the desired coating thickness or weight on the substrate. Likewise, coatings of several different types of washcoats can be applied to a substrate surface. The coated substrate is then heated to dry and calcine the coatings. Generally a temperature of about 700° C. for about 2-3 hours may be used. This method of calcining serves to develop the integrity of the ceramic structure of the washcoat oxide coating. The total amount of the oxide washcoat carried on the substrate is usually about 1 wt. % to 30 wt. % based on the substrate that is coated. As seen in the catalyst embodiments shown FIG. 3 through FIG. 6, the different metal oxide washcoat layers can be applied to the substrate in a variety of configurations.

At block 140 of FIG. 7, an overlay of one or more precious metals such as platinum, palladium or nickel is applied to the metal oxide coatings. In the embodiment shown in FIG. 3 through FIG. 5, the precious metals may be part of the metal oxide layer. In another embodiment, precious metals are part of the metal oxide layers as well as part of an overlay of the oxide layer with precious metals. According to another embodiment of the invention, the washcoated mixed metal oxide coating on the substrate is provided with at least about 2-15 g/ft$^3$ overlay of precious metal based on the volume of the substrate. In another, more preferred embodiment, a precious metal overlay is between approximately 2-10 g/ft$^3$. A total loading of precious metal on the oxide washcoat ranging between approximately 5-8 g/ft$^3$ is particularly preferred. It will be seen that there is a relatively high loading of rare earth metals and a relatively low loading of precious metals reducing cost yet providing good conversion efficiency and selectivity.

Finally, at block 350 of FIG. 7, a top coating of rhodium is applied to the precious metal overlay applied at block 340 or the mixed metal oxide if the precious metals were made part of the metal oxide. Rhodium acts as a broadening promoter to increase conversion efficiency.

In the examples shown in FIG. 3, FIG. 4 and FIG. 5, rhodium is incorporated with the $CeO_2+La_2O_3$ to decrease the overall amount of rhodium that is used.

The invention may be better understood with reference to the accompanying example, which is intended for purposes of illustration only and should not be construed as in any sense limiting the scope of the present invention as defined in the claims appended hereto.

Example 1

In order to demonstrate the selectivity and yield of products from syngas from the three stage combination of catalysts of the invention, the performance of various catalyst combinations within the stages were evaluated. Selected catalyst combinations were tested to show their performance for ethanol production in a reactor system modeled after the system shown in FIG. 1. The reactor stages and corresponding catalysts are designated (1), (2) and (3) in Table 1 and Table 2 and has the general composition and configuration described above. Table 2 has the results of a simulated reactor with product gas recycling at three different percentages of gas (75%, 90% and 99%).

The selectivity of the three stage reactor for the production of ethanol from syngas can be seen in the results shown in Table 1. For comparison, the results of synthesis gas over single and paired combinations of catalysts are shown. As indicated in Table 1, a Cu—Zn-alkali catalyst was used for catalyst component (1), an Rh—Y-alkali catalyst was used for catalyst component (2), and a Mo—Pd catalyst is used for catalyst component (3). Reaction conditions were the same for each combination of catalysts and the reactions took place at a temperature of 275° C. and a pressure of 700 psig. The feed syngas had a general composition of 66.6% $H_2$ and 33.3% CO. The gas hourly space velocity (GHSV) per hour and a summation of two carbon compounds are also indicated in Table 1.

Row A of Table 1 and Table 2, show the production of ethanol over the three stage catalysts of one embodiment of the invention. The catalyst performance including carbon conversion, selectivity and yield for ethanol and other products can be seen. The gas and liquid products produced for every 1000 liters of syngas feed of 66.6% $H_2$ and 33.3% CO at three different recycle percentages (75%, 90% and 99%) are shown in Table 2 illustrating the significant selectivity for ethanol and yield of the apparatus with recycling. As the percentage of product gas that is recycled increases, the selective production of ethanol substantially increases and the amount of reactant gases $H_2$ and CO are greatly reduced.

Row B of Table 1 and Table 2, contains the results of a reactor with catalyst component (1), a Cu—Zn-alkali catalyst, for comparison with the three stage catalyst of Row A. The reaction conditions were the same as with the three stage catalyst. It can be seen that the catalyst component (1) produces a very high yield of methanol (95.6%) and very little ethanol (1.4%). Recycling of the product gases through the catalyst improves the conversion efficiency of the CO and $H_2$ reactants to products.

Row C of Table 1, contains the results of a reactor with a single catalyst component (2), an Rh—Y-alkali catalyst, with the syngas feed. This single component (2) catalyst produces significant amounts of acetaldehyde (AcH) and lesser amounts of acetic acid (AcOH) and ethanol (EtOH). Recycling improves conversion efficiency of the reactant gases but insignificant amounts of ethanol are produced as seen in Row C of Table 2.

Combinations of paired components (1) and (2) as well as components (2) and (3) are shown in Row D and Row E of Table 1 and Table 2 for comparison with the single catalyst results and the results of the three stage catalyst of the invention. In Row D of Table 1 and Table 2, the results of representative catalyst components (1) and (2) are shown. A Cu—Zn-alkali catalyst is used for catalyst component (1) and an Rh—Y-alkali catalyst was used for catalyst component (2). This combination produced an increased yield of ethanol over the single catalysts alone. However, quantities of acetaldehyde (AcH) and acetic acid (AcOH) and water are produced as contaminants to the ethanol.

Row E of Table 1 and Table 2, show the results from a reactor with catalyst components (2) and (3). A Rh—Y-alkali catalyst was used for catalyst component (2) and a Mo—Pd catalyst was used for catalyst component (3). Ethanol yields are improved over the single catalysts described previously. However, the yield of ethanol is less than half of the yield of the three stage catalyst as seen in the results of Row E of Table 1.

Accordingly, the synergy resulting from the three catalyst components and the three stages can be seen in the selective production of liquid ethanol and useful product gases from the apparatus and associated processes. Recycling can greatly improve conversion efficiency for ethanol as well as methane. The process and apparatus can also be automated and industrialized.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

SYNTHESIS GAS TO ETHANOL OVER VARIOUS COMBINATIONS OF CATALYSTS

| Type: Component | Formulation | $GHSV^a$ $(hr^{-1})$ | CO $Conv^b$ (%) | Yield (Kg $L^{-1}$ $hr^{-1}$) | | | Carbon Selectivity (mol. %) | | | | |
|---|---|---|---|---|---|---|---|---|---|---|---|
| | | | | MeOH | EtOH | $\Sigma C_2{}^c$ | MeOH | EtOH | AcH | AcOH | $CH_4$ |
| A 3-way: | | | 30 | 30 | 282 | 293 | 5.2 | 68.7 | 0.6 | 1.6 | 18.4 |
| (1) | Cu—Zn-alkali | 9000 | | | | | | | | | |
| (2) | Rh—Y-alkali | 9000 | | | | | | | | | |
| (3) | Mo—Pd | 36000 | | | | | | | | | |
| B 1-way: | | | 20 | 820 | 9 | 9 | 95.6 | 1.4 | 0.0 | 0.0 | 0.1 |
| (1) | Cu—Zn-alkali | 9000 | | | | | | | | | |
| C 1-way: | | | 9 | 6 | 26 | 170 | 1.5 | 9.3 | 39.5 | 10.8 | 24.8 |
| (2) | Rh—Y-alkali | 9000 | | | | | | | | | |
| D 2-way: | | | 27 | 24 | 160 | 284 | 4.1 | 38.4 | 18.7 | 9.3 | 19.3 |
| (1) | Cu—Zn-alkali | 9000 | | | | | | | | | |
| (2) | Rh—Y—Li | 9000 | | | | | | | | | |
| E 2-way: | | | 10 | 3 | 116 | 139 | 0.9 | 47.2 | 2.1 | 5.4 | 25.4 |
| (2) | Rh—Y-alkali | 9000 | | | | | | | | | |
| (3) | Mo—Pd | 36000 | | | | | | | | | |

Reaction Conditions: Temperature of 275° C., Pressure of 700 psig, Syngas feed of 66.5% H2, 33.3% CO.
$^a$Gas hourly space velocity (at normal conditions) for each component and combination.
$^b$Overall CO conversion from syngas
$^c$Sum of all two carbon compounds
Abbreviations: MeOH: methanol, EtOH: ethanol, AcH: acetaldehyde, AcOH: acetic acid, $CH_4$: methane

TABLE 2

SYNTHESIS GAS TO ETHANOL FOR SIMULATED REACTOR WITH RECYCLE

| Ex. | Comp.$^a$ | $GHSV^b$ $(hr^{-1})$ | Recyc. Rate$^c$ (%) | Liquid Product (Kg/1000 L) | | | | | Gas Product (L/1000 L) | | | |
|---|---|---|---|---|---|---|---|---|---|---|---|---|
| | | | | MeOH | EtOH | AcH | AcOH | $H_2O$ | CO | $H_2$ | $CO_2$ | $CH_4$ |
| A | (1), (2), (3) | 4000 | 75 | 16 | 148 | 1 | 5 | 74 | 123 | 245 | 12 | 39 |
| A | (1), (2), (3) | 4000 | 90 | 20 | 191 | 2 | 6 | 96 | 63 | 126 | 15 | 50 |
| A | (1), (2), (3) | 4000 | 99 | 24 | 230 | 2 | 7 | 115 | 8 | 15 | 18 | 601 0/2 6/2 007 |
| B | (1) | 9000 | 75 | 228 | 2 | 0 | 0 | 5 | 167 | 333 | 0 | 0 |
| B | (1) | 9000 | 90 | 325 | 3 | 0 | 0 | 7 | 95 | 190 | 0 | 0 |
| B | (1) | 9000 | 99 | 438 | 5 | 0 | 0 | 10 | 13 | 26 | 0 | 0 |
| C | (2) | 9000 | 75 | 2 | 9 | 37 | 14 | 38 | 239 | 477 | 5 | 23 |
| C | (2) | 9000 | 90 | 4 | 16 | 64 | 24 | 67 | 167 | 335 | 9 | 41 |
| C | (2) | 9000 | 99 | 6 | 29 | 117 | 44 | 122 | 31 | 61 | 17 | 75 |
| D | (1), (2) | 4500 | 75 | 12 | 78 | 37 | 25 | 74 | 134 | 269 | 11 | 38 |
| D | (1), (2) | 4500 | 90 | 15 | 103 | 48 | 33 | 97 | 71 | 142 | 14 | 51 |
| D | (1), (2) | 4500 | 99 | 19 | 128 | 60 | 40 | 120 | 9 | 18 | 18 | 63 |
| E | (2), (3) | 7200 | 75 | 1 | 50 | 2 | 7 | 46 | 231 | 461 | 6 | 26 |

TABLE 2-continued

SYNTHESIS GAS TO ETHANOL FOR SIMULATED REACTOR WITH RECYCLE

| Ex. | Comp.[a] | GHSV[b] (hr$^{-1}$) | Recyc. Rate[c] (%) | Liquid Product (Kg/1000 L) | | | | | Gas Product (L/1000 L) | | | |
|---|---|---|---|---|---|---|---|---|---|---|---|---|
| | | | | MeOH | EtOH | AcH | AcOH | H$_2$O | CO | H$_2$ | CO$_2$ | CH$_4$ |
| E | (2), (3) | 7200 | 90 | 2 | 85 | 4 | 13 | 79 | 158 | 315 | 10 | 45 |
| E | (2), (3) | 7200 | 99 | 4 | 148 | 6 | 22 | 138 | 27 | 55 | 17 | 78 |

Reaction Conditions: Temperature of 275° C., Pressure of 700 psig, Syngas feed of 66.5% H2, 33.3% CO.
[a]Catalyst components making up the simulated catalyst. Components packed sequentially in a single reactor.
See Table I for formulations, conversion and selectivity data.
[b]Gas hourly space velocity (at normal conditions) for each component and combination
[c]Percentage of product gas that is recycled to the catalyst
Abbreviations: MeOH: methanol, EtOH: ethanol, AcH: acetaldehyde, AcOH: acetic acid, H2O: water, CO: carbon monoxide, H2: hydrogen, CO2: carbon dioxide, CH$_4$: methane.

What is claimed is:

1. A process of preparing an alcohol with two or more carbon atoms from a gas containing carbon monoxide and hydrogen, comprising:
    reacting a gas comprising carbon monoxide and hydrogen with a first catalyst configured to promote carbon monoxide hydrogenation;
    reacting said gas exposed to said first catalyst with a second catalyst configured to promote alcohol homologation; and
    reacting said gas exposed to said second catalyst with a third catalyst configured to promote hydrogenation of acid and aldehyde byproducts to alcohols,
    wherein said catalysts are separate catalysts used in series, and wherein said reactions occur under super-atmospheric temperature and pressure conditions.

2. A process as recited in claim 1, wherein said reaction pressure is between approximately 200 psig and approximately 2500 psig.

3. A process as recited in claim 1, wherein said reaction temperature is between approximately 150 degrees Celsius and approximately 400 degrees Celsius.

4. A process as recited in claim 1, wherein said hydrogenation catalyst is a catalyst selected from the group of catalysts consisting essentially of Cu, Zn, Mo, Ni, or Fe in free form.

5. A process as recited in claim 1, wherein said hydrogenation catalyst comprises copper in combination with Zn, Mo, Ni, or Fe.

6. A process as recited in claim 1, wherein said alcohol homologation catalyst comprises a Group VIII metal and yttrium metal.

7. A process as recited in claim 1, wherein said alcohol homologation catalyst comprises a combination of at least two Group VIII metals and yttrium metal.

8. A process as recited in claim 1, wherein said alcohol homologation catalyst comprises a Group VIII metal and a lanthanide series metal.

9. A process as recited in claim 1, wherein said alcohol homologation catalyst comprises a Group VIII metal and an actinide series metal.

10. A process as recited in claim 1, wherein said alcohol homologation catalyst comprises a combination of at least two Group VIII metals and a lanthanide series metal.

11. A process as recited in claim 1, wherein said alcohol homologation catalyst comprises a combination of at least two Group VIII metals and an actinide series metal.

12. A process as recited in claim 1, wherein said alcohol homologation catalyst comprises a combination of at least one Group VIII metal, an actinide series metal and a lanthanide series metal.

13. A process as recited in claim 1, wherein said hydrogenation catalyst further comprises an alkali metal promoter.

14. A process as recited in claim 1, wherein said hydrogenation catalyst further comprises a promoter, selected from the group of promoters consisting essentially of Ti, Zr, Pd, and Mn.

15. A process for the preparation of alcohols from a gas containing carbon monoxide and hydrogen, comprising:
    contacting a gas containing carbon monoxide and hydrogen with a first hydrogenation catalyst comprising Cu—Zn;
    contacting an outflow of gas from said first hydrogenation catalyst with a second carbonylation catalyst, said carbonylation catalyst comprising rhodium and a co-catalyst;
    contacting an outflow of gas from said carbonylation catalyst with a third hydrogenation catalyst and a promoter wherein said catalysts are separate catalysts used in series; and
    controlling the temperature and pressure of gas during contact with said catalysts.

16. A process as recited in claim 15, wherein said temperature is controlled to be at least 150 degrees and said pressure is controlled to be at least 200 psig.

17. A process as recited in claim 15, wherein said reaction temperature is controlled to between approximately 180 degrees Celsius and approximately 325 degrees Celsius and said reaction pressure is controlled to be between approximately 500 psig and approximately 1500 psig.

18. A process as recited in claim 15, wherein said co-catalyst is selected from the group of co-catalysts comprise consisting essentially of a lanthanide, an actinide and yttrium metal.

19. A process as recited in claim 15, wherein said second hydrogenation catalyst comprises Mo, Ni, or Fe.

20. A process as recited in claim 15, wherein said second catalyst promoter is a promoter, selected from a group of promoters consisting essentially of Ti, Zr, Pd, and Mn.

* * * * *